(12) United States Patent
Argentine

(10) Patent No.: US 8,454,682 B2
(45) Date of Patent: Jun. 4, 2013

(54) ANCHOR PIN STENT-GRAFT DELIVERY SYSTEM

(75) Inventor: Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 507 days.

(21) Appl. No.: 12/759,433

(22) Filed: Apr. 13, 2010

(65) Prior Publication Data
US 2011/0251667 A1 Oct. 13, 2011

(51) Int. Cl.
*A61F 2/82* (2006.01)

(52) U.S. Cl.
USPC ............................................. 623/1.36

(58) Field of Classification Search
USPC ...................... 623/1.14, 1.36, 1.15
See application file for complete search history.

(56) References Cited

U.S. PATENT DOCUMENTS

| | | | |
|---|---|---|---|
| 4,140,126 A | 2/1979 | Choudhury | |
| 5,158,548 A | 10/1992 | Lau et al. | |
| 5,207,695 A | 5/1993 | Trout, III | |
| 5,391,172 A | 2/1995 | Williams et al. | |
| 5,397,355 A | 3/1995 | Marin et al. | |
| 5,489,295 A | 2/1996 | Piplani et al. | |
| 5,514,154 A | 5/1996 | Lau et al. | |
| 5,562,726 A | 10/1996 | Chuter | |
| 5,562,728 A | 10/1996 | Lazarus et al. | |
| 5,567,728 A | 10/1996 | Noriender et al. | |
| 5,603,721 A | 2/1997 | Lau et al. | |
| 5,630,829 A | 5/1997 | Lauterjung | |
| 5,681,346 A | 10/1997 | Orth et al. | |
| 5,720,776 A | 2/1998 | Chuter et al. | |
| 5,728,158 A | 3/1998 | Lau et al. | |
| 5,733,325 A | 3/1998 | Robinson et al. | |
| 5,735,893 A | 4/1998 | Lau et al. | |
| 5,766,238 A | 6/1998 | Lau et al. | |
| 5,824,041 A | 10/1998 | Lenker et al. | |
| 5,843,167 A | 12/1998 | Dwyer et al. | |
| 5,855,601 A | 1/1999 | Bessler et al. | |
| 5,902,334 A * | 5/1999 | Dwyer et al. ................ 606/194 |
| 5,919,204 A | 7/1999 | Lukic et al. | |
| 5,925,061 A | 7/1999 | Ogi et al. | |

(Continued)

FOREIGN PATENT DOCUMENTS

| | | |
|---|---|---|
| FR | 2779939 | 6/1998 |
| WO | WO 96/18361 | 6/1996 |

(Continued)

OTHER PUBLICATIONS

U.S. Appl. No. 11/559,754, filed Nov. 14, 2006, Mitchell et al.

(Continued)

*Primary Examiner* — Thomas J Sweet
*Assistant Examiner* — Cheryl Miller

(57) ABSTRACT

A stent-graft delivery system includes a stent-graft including a proximal anchor stent ring. The proximal anchor stent ring includes proximal apexes and anchor pin structures extending proximally from each of the proximal apexes. The anchor pin structures include anchor pin connecting arms and anchor pins. The anchor pin structures are tucked together to accommodate small catheter sizes. Further, the anchor pins reduce or eliminate migration of the stent-graft. Further still, the anchor pin connecting arms are long and flexible thus distributing stresses in a way that improves the load carrying capacity of the anchor pins and allows flowering of the graft material of the stent-graft prior to release of the anchor pins structures.

21 Claims, 4 Drawing Sheets

U.S. PATENT DOCUMENTS

| | | | |
|---|---|---|---|
| 6,004,347 A | 12/1999 | McNamara et al. | |
| 6,056,776 A | 5/2000 | Lau et al. | |
| 6,066,167 A | 5/2000 | Lau et al. | |
| 6,066,168 A | 5/2000 | Lau et al. | |
| 6,077,297 A | 6/2000 | Robinson et al. | |
| 6,096,071 A | 8/2000 | Yadav | |
| 6,245,101 B1 | 6/2001 | Drasler et al. | |
| 6,254,632 B1 | 7/2001 | Wu et al. | |
| 6,287,335 B1 | 9/2001 | Drasler et al. | |
| 6,312,462 B1 | 11/2001 | McDermott et al. | |
| 6,319,276 B1 | 11/2001 | Holman et al. | |
| 6,395,017 B1 | 5/2002 | Dwyer et al. | |
| 6,395,019 B2 | 5/2002 | Chobotov | |
| 6,454,796 B1 * | 9/2002 | Barkman et al. | 623/1.35 |
| 6,517,573 B1 | 2/2003 | Pollock et al. | |
| 6,858,034 B1 | 2/2005 | Hijkema et al. | |
| 6,890,337 B2 | 5/2005 | Freeser et al. | |
| 7,004,964 B2 | 2/2006 | Thompson et al. | |
| 7,147,661 B2 | 12/2006 | Chobotov et al. | |
| 7,175,652 B2 | 2/2007 | Cook et al. | |
| 2002/0116048 A1 | 8/2002 | Chobotov | |
| 2003/0125797 A1 | 7/2003 | Chobotov et al. | |
| 2003/0135162 A1 | 7/2003 | Deyette et al. | |
| 2003/0158595 A1 | 8/2003 | Randall et al. | |
| 2004/0088044 A1 | 5/2004 | Brown et al. | |
| 2004/0093063 A1 | 5/2004 | Wright et al. | |
| 2004/0117003 A1 | 6/2004 | Ouriel et al. | |
| 2004/0153143 A1 | 8/2004 | Quiachon et al. | |
| 2005/0165441 A1 | 7/2005 | McGuckin et al. | |
| 2006/0161265 A1 * | 7/2006 | Levine et al. | 623/23.65 |
| 2007/0179591 A1 * | 8/2007 | Baker et al. | 623/1.23 |
| 2007/0250151 A1 | 10/2007 | Pereira | |
| 2008/0027529 A1 | 1/2008 | Hartley et al. | |
| 2008/0114442 A1 | 5/2008 | Mitchell et al. | |
| 2009/0082846 A1 | 3/2009 | Chobotov | |

FOREIGN PATENT DOCUMENTS

| | | |
|---|---|---|
| WO | WO01/17458 | 3/2001 |
| WO | WO03/053288 | 7/2003 |
| WO | WO2006/086313 | 8/2006 |

OTHER PUBLICATIONS

U.S. Appl. No. 11/559,765, filed Nov. 14, 2006, Mitchell et al.

* cited by examiner

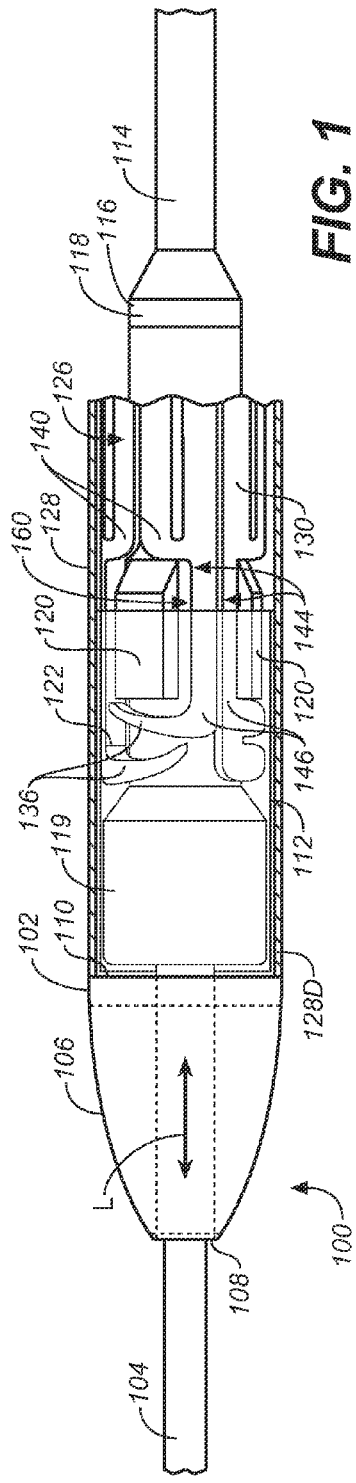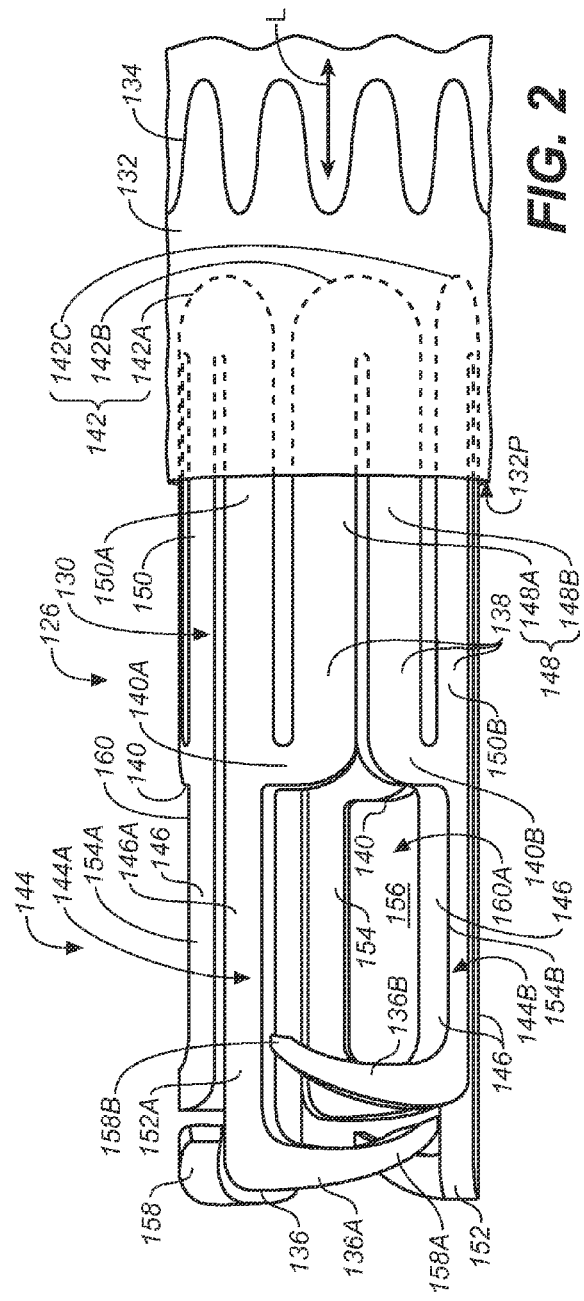

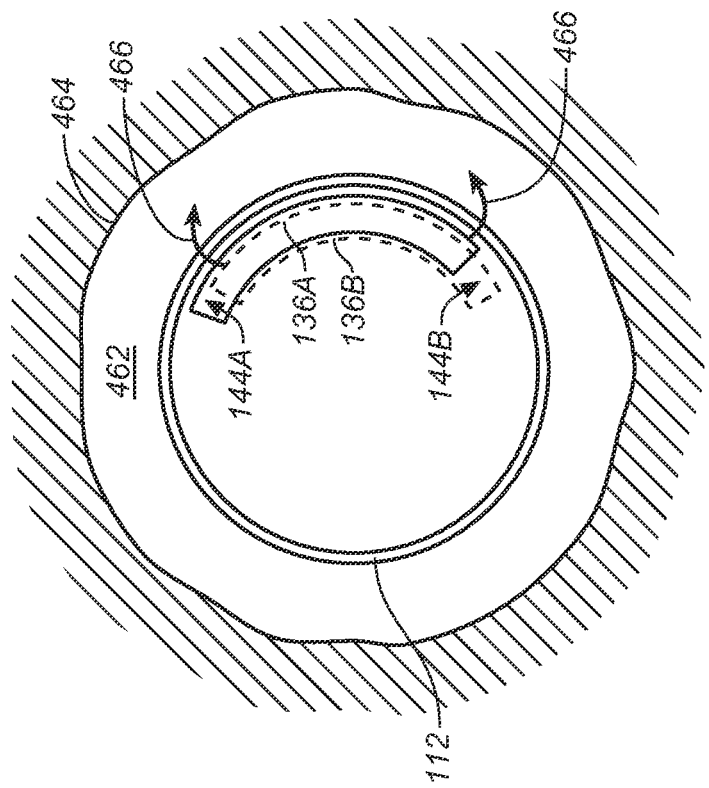
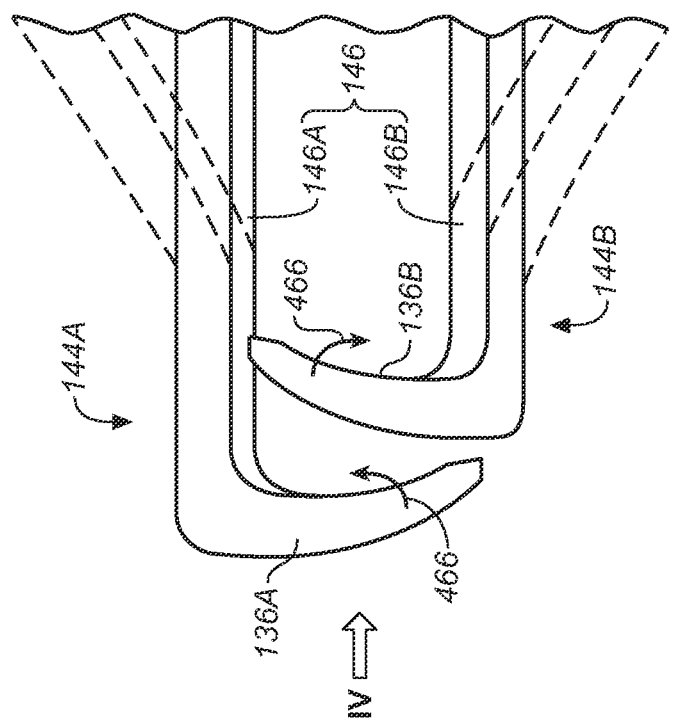

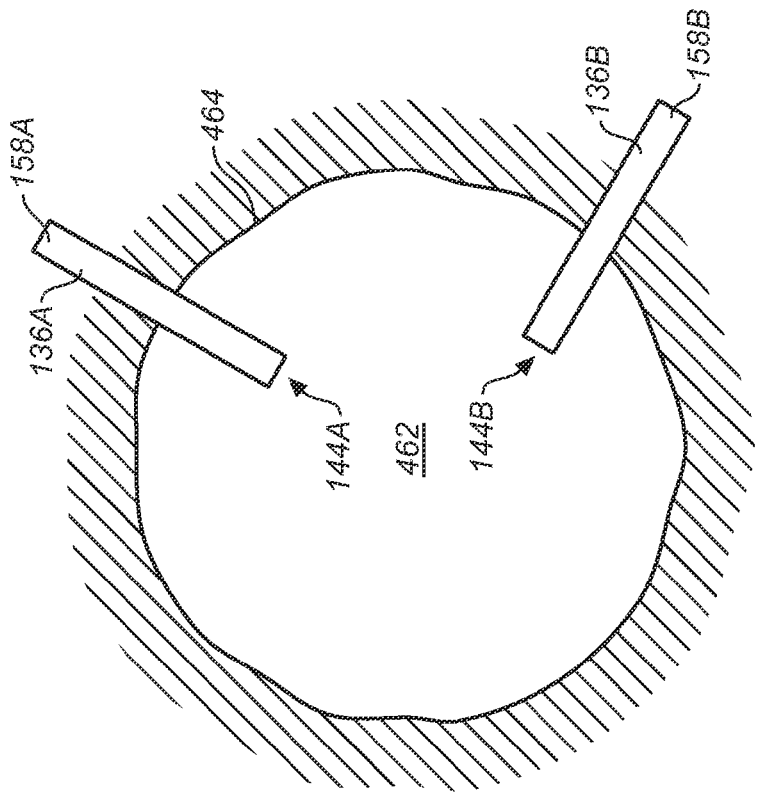
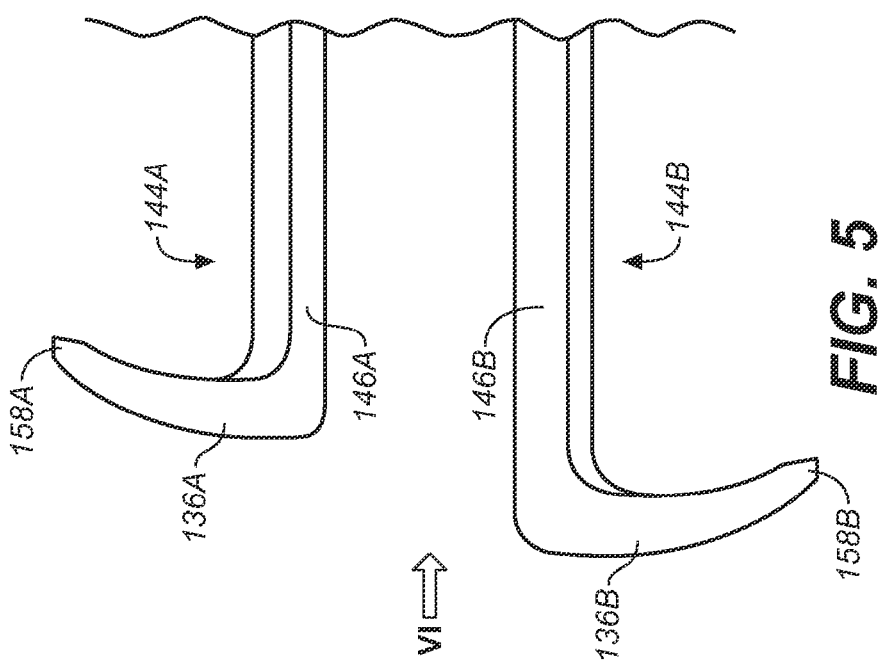
FIG. 6
FIG. 5

ANCHOR PIN STENT-GRAFT DELIVERY SYSTEM

BACKGROUND OF THE INVENTION

1. Field of the Invention

This invention relates generally to medical devices and procedures, and more particularly to a method and system of deploying a stent-graft in a vascular system and to the associated stent-graft.

2. Description of the Related Art

Prostheses for implantation in blood vessels or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass damaged or occluded natural blood vessels.

A graft material supported by a framework is known as a stent-graft or endoluminal graft. In general, the use of stent-grafts for treatment or isolation of vascular aneurysms and vessel walls which have been thinned or thickened by disease (endoluminal repair or exclusion) is well known.

Many stent-grafts, are "self-expanding", i.e., inserted into the vascular system in a compressed or contracted state, and permitted to expand upon removal of a restraint. Self-expanding stent-grafts typically employ a wire or tube configured (e.g., bent or cut) to act as a stent to provide an outward radial force and employ a suitable elastic material such as stainless steel or nitinol (nickel-titanium). Nitinol may additionally employ shape memory properties.

A self-expanding stent-graft is typically configured in a tubular shape shaped and sized for implantation at a slightly greater diameter than the diameter of the blood vessel in which the stent-graft is intended to be used. In general, rather than repair of aneurysms using open surgery which is traumatic and invasive, stents and stent-grafts are typically deployed through a less invasive intraluminal delivery, i.e., cutting through the skin to access a lumen or vasculature or percutaneously via successive dilatation, at a convenient (and less traumatic) entry point, and routing the stent-graft through the vascular lumen to the site where the prosthesis is to be deployed.

Intraluminal deployment in one example is effected using a delivery catheter with coaxial inner tube, sometimes called the plunger, and middle member, sometimes called the sheath, arranged for relative axial movement. The stent-graft is compressed and disposed within the distal end of the sheath in front of the majority of the inner tube.

The catheter is then maneuvered, typically routed though a lumen (e.g., vessel), until the end of the catheter (and the stent-graft) is positioned in the vicinity of the intended treatment site. The inner tube is then held stationary while the sheath of the delivery catheter is withdrawn. A stent stop attached to the inner tube prevents the stent-graft from moving back as the sheath is withdrawn.

As the sheath is withdrawn, the stent-graft is gradually exposed from a proximal end to a distal end of the stent-graft, the exposed portion of the stent-graft radially expands so that at least a portion of the expanded portion is in substantially conforming surface contact with a portion of the interior of the blood vessel wall.

The proximal end of the stent-graft is the end closest to the heart by way of blood flow path whereas the distal end is the end furthest away from the heart by way of blood flow path during deployment. In contrast and of note, the distal end of the catheter is usually identified as the end that is farthest from the operator (handle) while the proximal end of the catheter is the end nearest the operator (handle). For purposes of clarity of discussion, as used herein, the distal end of the catheter is the end that is farthest from the operator (the end furthest from the handle) while the distal end of the stent-graft is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system description may be consistent or opposite in actual usage.

SUMMARY OF THE INVENTION

In accordance with one example, a stent-graft delivery system includes a stent-graft including a proximal anchor stent ring. The proximal anchor stent ring includes proximal apexes and anchor pin structures extending proximally from each of the proximal apexes. The anchor pin structures include anchor pin connecting arms and anchor pins.

In one example, the anchor pin structures are tucked together to accommodate small catheter sizes. Further, the anchor pins reduce or eliminate migration of the stent-graft. Further still, the anchor pin connecting arms are long and flexible thus distributing stresses imposed on them at either end along their length in a way that improves larger lateral (hook like) structures ability to accommodate substantial load carrying by the anchor pins and allows flowering of the graft material of the stent-graft prior to release of the anchor pins structures.

These and other features will be more readily apparent from the detailed description set forth below taken in conjunction with the accompanying drawings.

BRIEF DESCRIPTION OF THE DRAWINGS

FIG. 1 is a partial schematicized see through view of a stent-graft delivery system in accordance with one embodiment;

FIG. 2 is a close up view of a stent-graft of the stent-graft delivery system of FIG. 1;

FIG. 3 is a side view of anchor pin structures of the stent-graft of FIG. 2 when the stent-graft is compressed in its delivery configuration;

FIG. 4 is an end view of the anchor pin structures viewed from the view identified from arrow IV of FIG. 3 including a sleeve located within a delivery system;

FIG. 5 is a side view of the anchor pin structures of FIG. 3 when the stent-graft is in its expanded configuration (after deployment);

FIG. 6 is an end view of the anchor pin structures viewed from arrow VI of FIG. 5 corresponding to the view of FIG. 4 after deployment within the vessel.

In the following description, the same or similar elements are labeled with the same or similar reference numbers.

DETAILED DESCRIPTION

Figure 7:
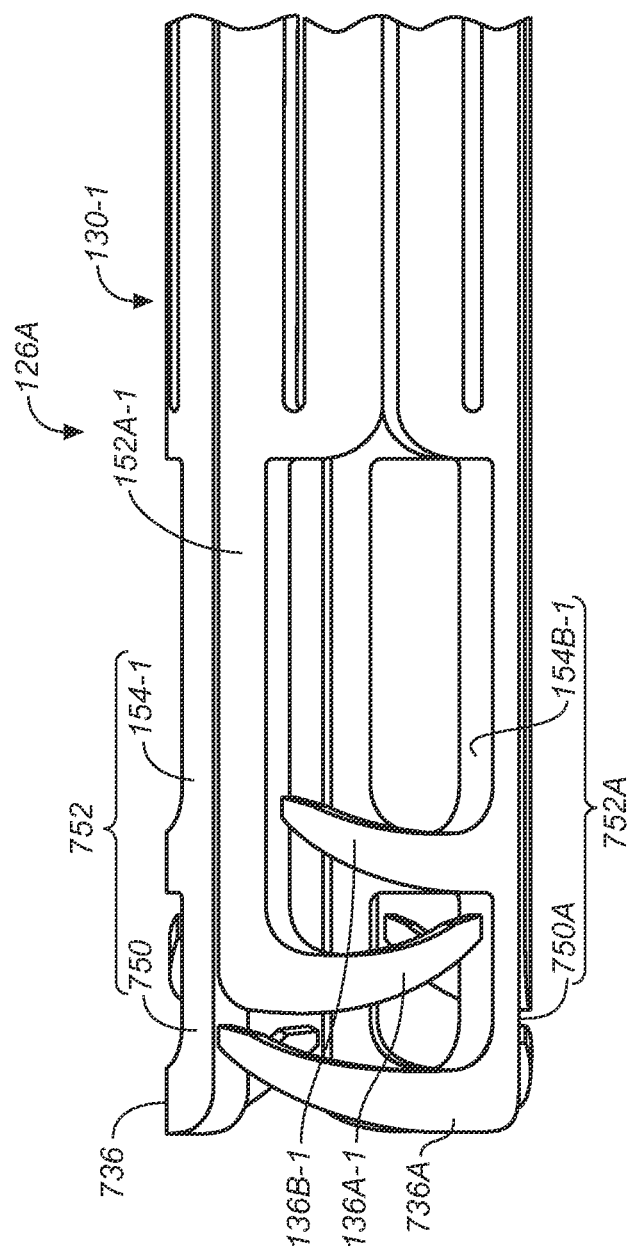
FIG. 7 is a close up view of a stent-graft in accordance with another example.

As an overview, referring to FIGS. 1 and 2 together, a stent-graft delivery system 100 includes a stent-graft 126 including a proximal anchor stent ring 130. Proximal anchor stent ring 130 includes proximal apexes 140 and anchor pin structures 144 extending proximally from each of proximal apexes 140. Anchor pin structures 144 include anchor pin connecting arms 146 and anchor pins 136.

In one example, anchor pin structures 144 are tucked together to accommodate small catheter sizes. Further, anchor pins 136 when deployed reduce or eliminate migration of stent-graft 126. Further still, anchor pin connecting arms 146 are long and flexible thus allowing torsional and bending stresses imposed by the anchor pin configuration to be distributed in a way that improves the penetration of the anchoring pins into the adjacent vessel wall to improve its load carrying capacity compared to less flexible and shorter hooks and allows flowering of a graft material 132 (stent graft material is shown in FIG. 2) of stent-graft 126 prior to release of anchor pins structures 144.

Now in more detail, FIG. 1 is a partial schematicized see through view of a stent-graft delivery system 100 in accordance with one embodiment. Stent-graft delivery system 100 includes a bullet tip 102, sometimes called a nosecone. Other tip shapes can also be used.

An inner tube 104 defines a lumen, e.g., a guide wire lumen, therein. Inner tube 104 is located within and is secured to bullet tip 102, i.e., bullet tip 102 is mounted on inner tube 104. The lumen of inner tube 104 allows a guide wire to be passed through inner tube 104 and bullet tip 102.

Bullet tip 102 includes a bullet like shaped tapered outer surface 106 that gradually increases in diameter. More particularly, tapered outer surface 106 has a minimum diameter at a distal end 108 and generally gradually increases in diameter proximally, i.e., in the direction of the operator (or handle of stent-graft delivery system 100), from distal end 108.

Tapered outer surface 106 extends proximally to a proximal end of the tip portion of the bullet tip 102. Primary sheath abutment shoulder 110 is an annular shelf perpendicular to a longitudinal axis "L" of stent-graft delivery system 100.

Bullet tip 102 further includes a sleeve 112 extending proximally from the proximal end of the tip portion of bullet tip. Generally, sleeve 112 is a hollow cylindrical tube, e.g., made of stainless steel, extending proximally and longitudinally from the proximal end of the bullet tip.

Stent-graft delivery system 100 further includes a middle member (tube) 114 having a spindle 116 located at and fixed to a distal end of middle member 114. Spindle 116, sometimes called a stent anchor, includes a spindle body 118 having a cylindrical outer surface and a plurality of spindle pins 120 protruding radially outward from spindle body 118.

As illustrated in FIG. 1, spindle 116 is configured to slip inside of sleeve 112 such that the ends of the spindle pins 120 are directly or closely adjacent to, or in contact with, the inner surface of sleeve 112. Spindle pins 120 extend from spindle body 118 towards and to sleeve 112. In one example, spindle 116 includes three and only three spindle pins 120. By minimizing the number of spindle pins 120 around the spindle body 118, the spindle pins 120 can be made very robust.

Generally, the diameter to which spindle pins 120 extend from spindle body 118 is approximately equal to, or slightly less than, the inner diameter of sleeve 112 allowing spindle pins 120 to snugly fit inside of sleeve 112. An annular space 122 exists between the inside surface of sleeve 112 and the outside surface of spindle body 118. The distal end of spindle 116 includes a tip stop 119 fixed to or integral with the spindle body 118 to prevent the anchor pins 136 from sliding toward the bullet tip 102 when bullet tip 102 and sleeve 112 are moved forward to release the anchor pins 136.

Inner tube 104 is within and extends through middle member 114 and spindle 116. Inner tube 104 and thus bullet tip 102 is moved along longitudinal axis L (longitudinally moved) relative to middle member 114 and thus spindle 116 to release a proximal end of a stent-graft 126 as discussed further below. Stent-graft 126 is located within a retractable primary sheath 128 in a pre-deployment position (when sheath 128 is not yet retracted). The term "stent-graft" used herein should be understood to include stent-grafts and other forms of endoprosthesis.

FIG. 2 is a close up view of stent-graft 126 of stent-graft delivery system 100 of FIG. 1. In FIG. 1, the distal end of stent-graft 126 and the proximal end of retractable primary sheath 128 are cutaway to illustrate middle member 114 and spindle body 118. Further, sleeve 112, and retractable primary sheath 128 are transparent in the view of FIG. 1 to allow visualization of the elements therein although sleeve 112 and retractable primary sheath 128 are schematically shown in other examples.

Referring now to FIGS. 1 and 2 together, retractable primary sheath 128 is a hollow tube and defines a lumen therein containing middle member 114 and inner tube 104. Retractable primary sheath 128 is pictured in a pre-deployment position in FIG. 1. Retractable primary sheath 128 is moved proximally with respect to the delivery system along longitudinal axis "L", sometimes called retracted, relative to middle member 114, spindle 116, and stent-graft 126 to deploy a portion of stent-graft 126 as discussed further below. In one example, stent-graft 126 is a self-expanding stent-graft such that stent-graft 126 self-expands upon being released from its radially constrained configuration.

Stent-graft 126 in a radially constrained configuration surrounds a portion of middle member 114 and spindle 116. Stent-graft 126 is located within and is held radially compressed by retractable primary sheath 128. Further, a proximal anchor stent ring 130, sometimes called the proximal tip, of stent-graft 126 is radially constrained and held in position in annular space 122 between the outer surface of spindle body 118 and the inner surface of sleeve 112. Proximal anchor stent ring 130 is at the proximal end of stent-graft 126.

Stent-graft 126 includes a graft material 132, e.g., formed of polyester or Dacron material. The edges of graft material 132 are represented by dashed lines in FIG. 2. Proximal anchor stent ring 130 is attached to a proximal end 132P of graft material 132 by, for example, stitching.

Stent-graft 126 further includes one or more resilient self-expanding stent rings 134, e.g., formed of super elastic self-expanding memory material such as nitinol, attached to graft material 132. Proximal anchor stent ring 130 and stent rings 134 are attached to graft material 132, e.g., by sutures, adhesive, or other means. Graft material 132 and stent rings 134 are radially constrained by retractable primary sheath 128 (not shown in FIG. 2).

Typically, stent-graft 126 is deployed such that graft material 132 spans, sometimes called excludes, a diseased portion of the vessel, e.g., an aneurysm. Further, proximal anchor stent ring 130, e.g., a suprarenal stent structure, is typically engaged with a healthy portion of the vessel adjacent the diseased portion, the healthy portion having stronger tissue than the diseased portion. By forming proximal anchor stent ring 130 with anchor pins 136 as discussed below, the anchor pins 136 penetrate (land) into the vessel wall of the healthy tissue thus anchoring proximal anchor stent ring 130 to strong tissue.

Generally, graft material 132 of stent-graft 126 and stent rings 134 attached to it are held radially constrained by retractable primary sheath 128 and the proximal portion of proximal anchor stent ring 130 is held radially constrained by sleeve 112 allowing for sequential, selective, and independent initial deployment of graft material 132 followed by subsequent deployment of proximal anchor stent ring 130 of stent-graft 126.

Retractable primary sheath 128 includes a distal end 128D adjacent to or in abutting contact with primary sheath abutment shoulder 110 of bullet tip 102. Distal end 128D fits snugly around sleeve 112 and in one example lightly presses radially inward on sleeve 112.

Proximal anchor stent ring 130 includes a zigzag pattern of struts 138 alternating between proximal apexes 140 and distal apexes 142. Distal apexes 142 are attached to graft material 132 of stent-graft 126.

Proximal anchor stent ring 130 further includes anchor pin structures 144. More particularly, an anchor pin structure 144 extends proximally from each proximal apex 140. To illustrate, a first anchor pin structure 144A of the plurality of anchor pin structures 144 extends proximally from a first proximal apex 140A of the plurality of proximal apexes 140. Further, a second anchor pin structure 144B of the plurality of anchor pin structures 144 extends proximally from a second proximal apex 140B of the plurality of proximal apexes 140.

Anchor pin structures 144 include anchor pin connecting arms 146 and anchor pins 136. To illustrate, first anchor pin structure 144A includes a first anchor pin connecting arm 146A of the plurality of anchor pin connecting arms 146 and a first anchor pin 136A of the plurality of anchor pins 136. Further, second anchor pin structure 144B includes a second anchor pin connecting arm 146B of the plurality of anchor pin connecting arms 146 and a second anchor pin 136B of the plurality of anchor pins 136.

As discussed in greater detail below, anchor pin structures 144 are tucked together to accommodate small catheter sizes. Further, anchor pins 136 when deployed reduce or eliminate migration of stent-graft 126. Further still, anchor pin connecting arms 146 are long and flexible thus reducing point stresses and distributing stresses over their length to improve the load carrying capacity of anchor pins 136 when compared to other shorter and resultingly less flexible anchor pins. The long arms also promote and allow flowering of graft material 132 prior to release of anchor pins structures 144.

Struts 138 include offset struts 148 and aligned struts 150. Offset struts 148 are identical with aligned struts 150, i.e., struts 138 are all identical in structure. The distinction between an offset strut 148 and an aligned strut 150 is dependent upon the relationship with anchor pin connecting arms 146.

More particularly, an offset strut 148 extends directly between a proximal apex 140 and a distal apex 142 and does not lie upon a common line with an anchor pin connecting arm 146. Stated another way, an offset strut 148 is circumferentially offset from an anchor pin connecting arm 146. To illustrate, first and second offset struts 148A, 148B of the plurality of offset struts 148 are circumferentially offset from anchor pin connecting arms 146.

In contrast, an aligned strut 150 lies upon a common line with an anchor pin connecting arm 146. Stated another way, an aligned strut 150 is circumferentially positioned so that the strut longitudinal axis is generally aligned with a longitudinal axis of an anchor pin connecting arm 146 (circumferentially aligned). To illustrate, first and second aligned struts 150A, 150B of the plurality of aligned struts 150 are circumferentially aligned with first and second anchor pin connecting arms 146A, 146B, respectively. More particularly, first anchor pin connecting arm 146A is a proximal extension of first aligned strut 150A. Similarly, second anchor pin connecting arm 146B is a proximal extension of second aligned strut 150B.

In accordance with this example, proximal anchor stent ring 130 includes a repeating pattern of offset struts 148 and aligned struts 150. More particularly, proximal anchor stent ring 130 includes a pair (two) offset struts 148, a pair of aligned struts 150, a pair of offset struts 148, a pair of aligned struts 150, a pair of offset struts 148, and a pair of aligned struts 150, for a total of twelve struts 138. Although proximal anchor stent ring 130 is set forth as including twelve struts 138, in other examples, a similar proximal anchor stent ring includes more or less than twelve struts.

The repeating pattern of offset struts 148 and aligned struts 150 results in distal apexes 142 being connected to either a pair of offset struts 148 or a pair of aligned struts 150. More particularly, every other distal apex 142 is connected to a pair of aligned struts 150 and the distal apex 142 in between is connected to a pair of offset struts 148. To illustrate, distal apexes 142 include first, second, and third distal apexes 142A, 142B, 142C. First and third distal apexes 142A, 142C are connected to aligned struts 150 (including first and second aligned struts 150A, 150B). Second distal apex 142B is between first and third distal apexes 142A, 142C and is connected to offset struts 148, i.e., first and second offset struts 148A, 148B.

Further, anchor pin connecting arms 146 include anchor pin connecting long arms 152 and anchor pin connecting short arms 154. Long arms 152 are longer than short arms 154. The use of long arms 152 and short arms 154 longitudinally offsets and eliminates the interference between adjacent anchor pins 136 allowing immediately adjacent and potentially interfering anchor pins 136 to be tucked one beneath the other as illustrated. Tucking anchor pins 136 enables proximal anchor stent ring 130 to be compressed to an extremely small size thus accommodating small catheter sizes.

In accordance with this example, proximal anchor stent ring 130 includes an alternating pattern of long arms 152 and short arms 154. More particularly, proximal anchor stent ring 130 includes a long arm 152, a short arm 154, a long arm 152, a short arm 154, a long arm 152, and a short arm 154, for a total of three long arms 152 and three short arms 154. Stated another way, a long arm 152 is between short arms 154 and vice versa. Although proximal anchor stent ring 130 is set forth as including three long arms 152 and three short arms 154, in other examples, a similar proximal anchor stent ring includes more or less than three long arms and three short arms.

Further, each long arm 152 is directly adjacent one respective short arm, e.g., 154, in a first circumferential direction and spaced apart from a second respective short arm, e.g., 154, in an opposite second circumferential direction.

To illustrate, a first long arm 152A of the plurality of long arms 152 is directly adjacent a first short arm 154A of the plurality of short arms 154. More particularly, the distance between first long arm 152A and first short arm 154A, sometimes called the adjacent first short arm 154A, is approximately equal to the distance between adjacent struts, e.g., 138, when in a compressed configuration.

Further, first long arm 152A is spaced apart from a second short arm 154B of the plurality of short arms 154 by a space 156. More particularly, space 156 between first long arm 152A and second short arm 154B, sometimes called the spaced apart second short arm 154B, has a circumferential width approximately equal to two times the circumferential width of struts 138, i.e., the width of first and second offset struts 148A, 148B, plus three times the circumferential distance between struts 138 when in a compressed configuration.

Similarly, each short arm 154 is directly adjacent the respective long arm 152 in the second circumferential direction and spaced apart from the respective long arm 152 in the opposite first circumferential direction.

Anchor pins 136 are connected to the proximal ends of anchor pin connecting arms 146. Distal ends of anchor pin connecting arms 146 are connected to proximal apexes 140.

In the delivery configuration (sometimes called delivery profile, the compressed configuration, or the unexpanded configuration) of proximal anchor stent ring 130, anchor pins 136 lie upon the longitudinal extension of the imaginary cylindrical surface defined by the inner surface of the zigzag pattern of struts 138 alternating between proximal apexes 140 and distal apexes 142. Further, in the delivery configuration, anchor pins 136 extend in a generally circumferential direction from anchor pin connecting arms 146. Anchor pins 136 may not extend exactly in a circumferential direction, i.e., may not extend exactly in a 90° angle from anchor pin connecting arms 146. In one example, anchor pins 136 extend at an 80° angle from anchor pin connecting arms 146, i.e., the angle between anchor pins 136 and anchor pin connecting arms 146 is 80°.

As used herein, a circumferential direction is the curved arc path along the perimeter of a circle defined by the intersection of a plane perpendicular to longitudinal axis "L" and an imaginary cylindrical surface defined by and projecting from the zigzag pattern of struts 138. Further, the longitudinal direction is the direction parallel to longitudinal axis L of stent-graft 126 and delivery system 100.

As anchor pin connecting arms 146 extend generally in the longitudinal direction whereas anchor pins 136 extend generally in a circumferential direction, or approximately so, the length of anchor pins 136 is perpendicular, or approximately so, to the length of anchor pin connecting arms 146.

Each anchor pin 136 extends from one anchor pin connecting arm towards an adjacent spaced apart anchor pin connecting arm. To illustrate, first anchor pin 136A extends from first long arm 152A towards spaced apart second short arm 154B. Second anchor pin 136B extends from second short arm 154B towards spaced apart first long arm 152A.

Second anchor pin 136B extends in a first circumferential direction whereas first anchor pin 136A extends in the opposite second circumferential direction. As discussed above, due to the difference in longitudinal length between first long arm 152A and second short arm 154B, first anchor pin 136A is longitudinally offset from second anchor pin 136B. More particularly, second anchor pin 136B is distal to (to the right of, as pictured in FIG. 2) first anchor pin 136A allowing second anchor pin 136B to be tucked distally to first anchor pin 136A.

Anchor pins 136 end with sharp points 158, which facilitate penetration of anchor pins 136 into the wall of the vessel in which stent-graft 126 is deployed. To illustrate, first and second anchor pins 136A, 136B include first and second sharp points 158A, 158B, respectively.

Sharp points 158 are located adjacent to the respective spaced apart anchor pin connecting arms 146. To illustrate, first sharp point 158A is adjacent to second short arm 154B and second sharp point 158B is adjacent to first long arm 152A.

In its unexpanded configuration, proximal apexes 140, anchor pins 136, and anchor pin connecting arms 146 define spindle pin catches (openings) 160. Spindle pin catches 160 are pockets, sometimes called openings or holes, which surround radially extending spindle pins 120 of stent-graft delivery system 100 to longitudinally and circumferentially constrain the position of proximal anchor stent ring 130 in its unexpanded configuration (crimped/compressed profile) prior to deployment as discussed in greater detail below.

To illustrate, referring to a first spindle pin catch 160A of the plurality of spindle pin catches 160, first and second proximal apexes 140A, 140B define the distal circumferential edge of first spindle pin catch 160A. First long arm 152A and second short arm 154B define the longitudinal edges of first spindle pin catch 160A. Finally, second anchor pin 136B defines the proximal circumferential edge of first spindle pin catch 160A.

Illustratively, proximal anchor stent ring 130 is laser cut from a one-piece material, e.g., nitinol, such as a tube. After being cut, proximal anchor stent ring 130 is sequentially expanded, e.g., using a mandrel, and heat set, into its final expanded configuration as those of skill in the art will understand in light of this disclosure. In one example, the mandrel includes protruding features which facilitate heat setting of anchor pins 136 in their outward extending position.

Further, as proximal anchor stent ring 130 is integral in one example, i.e., is a single piece laser cut from a tube and not a plurality of separate pieces attached together, anchor pins 136 are durable, e.g., are not likely to break off or otherwise fail. Further, by forming anchor pin connecting arms 146 to have a significant length and flexibility, stresses are distributed throughout anchor pin connecting arms 146 thus improving the load carrying capacity of anchor pins 136. For example, long arms 152 are 0.160 inches long and short arms 154 are 0.125 inches long. For comparison, in one example, anchor pins 136 are 0.050 or 0.040 inches long, the outer diameter of proximal anchor stent ring 130 is 0.128 inches before deployment, e.g., the outer diameter of the tube from which proximal anchor stent ring 130 is cut is 0.128 inches, and the thickness of proximal anchor stent ring 130 is 0.008 inches, e.g., the thickness of the tube from which proximal anchor stent ring 130 is cut is 0.008 inches.

FIG. 3 is a side view of first and second anchor pin structures 144A, 144B of stent-graft 126 of FIG. 2 when stent-graft 126 is in the compressed delivery configuration. FIG. 4 is an end view of first and second anchor pin structures 144A, 144B viewed from the arrow IV of FIG. 3 including a depiction of sleeve 112 located within a vessel lumen 462 having a vessel wall 464. In FIG. 4, only sleeve 112 and first and second anchor pin structures 144A, 144B of stent-graft delivery system 100 are illustrated for simplicity. However, it is to be understood that additional anchor pin structures, e.g., 144, and other elements of stent-graft delivery system 100 would ordinarily be visible in the view of FIG. 4. Further, the part of second anchor pin 136B which can be seen in this view is illustrated in dashed lines to highlight the distinction between second anchor pin 136B and first anchor pin 136A.

Referring now to FIGS. 1, 2, 3, and 4 together, to initiate deployment of stent-graft 126, retractable primary sheath 128 is partially or completely retracted such that distal end 128D is spaced apart from bullet tip 102. Due to the retraction of retractable primary sheath 128, the distal portion of stent-graft 126 is exposed and partially or completely deployed.

However, anchor pin structures 144 continue to be restrained within annular space 122 between sleeve 112 and spindle body 118. More particularly, anchor pins 136 and the proximal portion of anchor pin connecting arms 146 are restrained within annular space 122 between sleeve 112 and spindle body 118. As the distal portion of anchor pin connecting arms 146 are released by retractable primary sheath 128, the proximal portion of anchor pin connecting arms 146 allow for the initial and partial expansion of the distal portion of proximal anchor stent ring 130, the configuration of which is shown by dashed lines in FIG. 3. Stated another way, anchor pin connecting arms 146 are flexible thus allowing for flowering (self expansion) of stent rings 134 including graft material 132 attached thereto.

Once stent-graft 126 is properly positioned and retractable primary sheath 128 has been partially or completely retracted, proximal anchor stent ring 130 is released and deployed by advancing sleeve 112 as discussed further below thus partially securing stent-graft 126 in position within vessel lumen 462. More particularly, upon complete release of proximal anchor stent ring 130 and its anchor pins 136, first and second anchor pins 136A, 136B turn out from their original circumferential direction to extend radially outward in the direction indicated by the arrows 466 in FIGS. 3, 4 and as discussed in greater detail below. As used herein, the radial direction is a direction perpendicular to the imaginary cylindrical surface defined by the zigzag pattern of struts 138, as earlier discussed and passing through the longitudinal centerline of the stent graft.

FIG. 5 is a side view of anchor pin structures 144A, 144B of FIG. 3 when stent-graft 126 is in its expanded configuration (after deployment). FIG. 6 is an end view of first and second anchor pin structures 144A, 144B viewed from arrow VI of FIG. 5 corresponding to the view of FIG. 4 after deployment within vessel lumen 462.

Referring now to FIGS. 1, 5 and 6 together, bullet tip 102 including sleeve 112 is advanced relative to spindle 116 to expose anchor pin structures 144. More particularly, anchor pins 136 and the proximal portion of anchor pin connecting arms 146 are released from annular space 122 between sleeve 112 and spindle body 118. As anchor pins 136 extend in the circumferential direction while constrained by sleeve 112 and are not aligned with the longitudinal motion (advancement) of sleeve 112, anchor pins 136 do not dig into sleeve 112 allowing easy advancement of sleeve 112. Upon being released from sleeve 112 of bullet tip 102, the proximal portion of proximal anchor stent ring 130 (including anchor pins 136 and the proximal portion of anchor pin connecting arms 146) self-expands to and into vessel wall 464 of vessel lumen 462 in which stent-graft 126 is being deployed.

Once deployed, anchor pins 136A, 136B straighten to protrude radially outward from the imaginary cylindrical surface defined by the zigzag pattern of struts 138. Generally, first and second anchor pins 136A, 136B protrude radially outward from proximal anchor stent ring 130 and specifically from anchor pin connecting arms 146. Generally, all of the rotation that causes first and second anchor pins 136A, 136B to rotate from the circumferential direction to the radial direction occurs in the first and second anchor pin connecting arms 146A, 146B.

By protruding radially outwards from proximal anchor stent ring 130, first and second anchor pins 136A, 136B, i.e., first and second sharp points 158A, 158B thereof, penetrate into vessel wall 464 thus anchoring proximal anchor stent ring 130 and stent-graft 126 to vessel wall 464. In this manner, migration of stent-graft 126 is reduced or eliminated.

FIG. 7 is a close up view of a proximal portion of a stent-graft 126A in accordance with another example. Stent-graft 126A of FIG. 7 is similar to stent-graft 126 of FIG. 2. More particularly, stent-graft 126A includes a proximal anchor stent ring 130-1, anchor pins including first and second anchor pins 136A-1, 136B-1, struts, proximal apexes, anchor pin structures, anchor pin connecting arms, offset struts, aligned struts, long arms including a long arm 152A-1, shorts arms 154-1 including a short arm 154B-1, spaces, sharp points, and spindle pin catches similar or identical to proximal anchor stent ring 130, anchor pins 136 including anchor pins 136A, 136B, struts 138, proximal apexes 140, anchor pin structures 144, anchor pin connecting arms 146, offset struts 148, aligned struts 150, long arms 152 including first long arm 152A, shorts arms 154 including second short arm 154B, spaces 156, sharp points 158, and spindle pin catches 160 of stent-graft 126 of FIG. 2, respectively.

Referring now to FIG. 7, stent-graft 126A includes short arm extensions 750 including a first short arm extension 750A and anchor pins 736, sometimes called extension anchor pins, including a first anchor pin 736A. Short arm extensions 750 are proximal extensions and lie upon circumferential surface in line with short arms 154-1. Short arm extensions 750 and short arms 154-1 form double anchor pin arms 752 including a first double anchor pin arm 752A.

To illustrate, short arm extension 750A is a proximal extension and lies upon a circumferential surface in line with short arm 154B-1. Short arm extension 750A and short arm 154B-1 form double anchor pin arm 752A. Double anchor pin arm 752A is longer than long arm 152A-1.

First anchor pin 736A is connected to the proximal end of short arm extension 750A. Further, second anchor pin 136B-1 is connected between the proximal end and the distal end of double anchor pin arm 752A. In the following discussion, first and second anchor pins 736A, 136B-1, short arm extension 750A, and double anchor pin arm 752A are discussed, however, it is to be understood that the discussion is equally applicable to the other anchor pins, short arm extensions, and double anchor pin arms of proximal anchor stent ring 130-1.

In the delivery configuration of proximal anchor stent ring 130-1, first anchor pin 736A lies upon the imaginary cylindrical surface defined by the inner surface of the zigzag pattern of struts alternating between the proximal apexes and the distal apexes of proximal anchor stent ring 130-1. Further, in the delivery configuration, first anchor pin 736A extends in a generally circumferential direction from short arm extension 750A.

As short arm extension 750A extends generally in the longitudinal direction whereas first anchor pin 736A extends generally in a circumferential direction, or approximately so, the length of first anchor pin 736A is perpendicular, or approximately so, to the length of short arm extension 750A.

First anchor pin 736A and second anchor pin 136B-1 connected to double anchor pin arm 752A extend in the same circumferential direction from double anchor pin arm 752A.

In a manner similar to that discussed above, due to the difference in longitudinal length between long arm 152A-1 and short arm 154B-1, third anchor pin 136A-1 is longitudinally offset from second anchor pin 136B-1. More particularly, second anchor pin 136B-1 is distal to (to the right of, as pictured in FIG. 7) third anchor pin 136A-1 allowing second anchor pin 136B-1 to be tucked distally to third anchor pin 136A-1. Further, due to the greater longitudinal length of double anchor pin arm 752A greater than long arm 152A-1, first anchor pin 736A is longitudinally offset from anchor pin 136A-1. More particularly, first anchor pin 736A is proximal to (to the left of, as pictured in FIG. 7) third anchor pin 136A-1 allowing third anchor pin 136A-1 to be tucked distally to anchor pin 736A. Generally, third anchor pin 136A-1 is longitudinally sandwiched between first anchor pin 736A and second anchor pin 136B-1.

Upon being deployed, first anchor pin 736A penetrates into the vessel wall, in addition to second anchor pin 136B-1. Thus, first anchor pin 736A provides extra fixation of stent-graft 126A further preventing migration of stent-grant 126A.

In one example, third and second anchor pins 136A-1, 136B-1, e.g., 0.040 inches long, are shorter than first anchor pin 736A, e.g., 0.050 inches long.

The drawings and the forgoing description provide examples according to the present invention, and are however, by no means limited by these specific examples. Numerous variations, whether explicitly given in the specification or not, such as differences in structure, dimension, and use of material, are possible.

What is claimed is:

1. A stent-graft delivery system comprising:
a stent-graft comprising a proximal anchor stent ring comprising:
proximal apexes;
anchor pin structures extending proximally from each of said proximal apexes, said anchor pin structures comprising anchor pin connecting arms and anchor pins, said anchor pin connecting arms comprising:
anchor pin connecting long arms;
anchor pin connecting short arms, said anchor pin connecting long arms being longer than said anchor pin connecting short arms;
distal apexes; and
struts alternating between said proximal apexes and said distal apexes, wherein said struts comprise:
offset struts; and
aligned struts;
wherein every other of said distal apexes is connected to a pair of said aligned struts, wherein the distal apexes between said every other of said distal apexes is connected to a pair of said offset struts.

2. The stent-graft delivery system of claim 1 wherein said stent-graft further comprises:
graft material attached to said distal apexes.

3. The stent-graft delivery system of claim 1 4 wherein said offset struts are circumferentially offset from said anchor pin connecting arms.

4. The stent-graft delivery system of claim 1 4 wherein said aligned struts are circumferentially aligned with said anchor pin connecting arms.

5. The stent-graft delivery system of claim 1 4 wherein said anchor pin connecting arms are proximal extensions of said aligned struts.

6. The stent-graft delivery system of claim 1 4 wherein said proximal anchor stent ring comprises a repeating pattern of said offset struts and said aligned struts.

7. The stent-graft delivery system of claim 1 4 wherein said distal apexes are connected to either a pair of said offset struts or a pair of said aligned struts.

8. The stent-graft delivery system of claim 1 wherein said anchor pin connecting long arms and said anchor pin connecting short arms longitudinally offset said anchor pins.

9. The stent-graft delivery system of claim 8 wherein said proximal anchor stent ring comprises an alternating pattern of said anchor pin connecting long arms and said anchor pin connecting short arms.

10. The stent-graft delivery system of claim 9 wherein said anchor pin connecting short arms are between said anchor pin connecting long arms.

11. The stent-graft delivery system of claim 8 wherein each of said anchor pin connecting long arms is directly adjacent an adjacent anchor pin connecting short arm in a first circumferential direction and is spaced apart from a spaced apart anchor pin connecting short arm in an opposite second circumferential direction.

12. The stent-graft delivery system of claim 11 wherein a distance between an anchor pin connecting long arm and an adjacent anchor pin connecting short arm is equal to a distance between said struts.

13. The stent-graft delivery system of claim 11 wherein a distance between an anchor pin connecting long arm and a spaced apart anchor pin connecting short arm is equal to two times a width of said struts plus three times a distance between said struts.

14. The stent-graft delivery system of claim 1 wherein said proximal anchor stent ring further comprises:
short arm extensions extending proximally from said anchor pin connecting short arms; and
extension anchor pins connected to proximal ends of said short arm extensions.

15. The stent-graft delivery system of claim 1 wherein said anchor pins are connected to proximal ends of said anchor pin connecting arms.

16. The stent-graft delivery system of claim 1 wherein said anchor pins comprise sharp points.

17. A stent-graft comprising:
a proximal anchor stent ring comprising:
proximal apexes;
distal apexes;
anchor pin structures extending proximally from each of said proximal apexes, said anchor pin structures comprising anchor pin connecting arms and anchor pins;
struts alternating between said proximal apexes and said distal apexes, said struts comprising:
offset struts circumferentially offset from said anchor pin connecting arms;
aligned struts circumferentially aligned with said anchor pin connecting arms, wherein said anchor pin connecting arms are proximal extensions of said aligned struts;
a graft material attached to said distal apexes
wherein said anchor pin connecting arms comprise:
anchor pin connecting long arms; and
anchor pin connecting short arms, said anchor pin connecting long arms being longer than said anchor pin connecting short arms;
wherein each of said anchor pin connecting long arms is directly adjacent an adjacent anchor pin connecting short arm in a first circumferential direction and is spaced apart from a spaced apart anchor in connecting short arm in an opposite second circumferential direction;
wherein a distance between an anchor pin connecting long arm and a spaced apart anchor pin connecting short arm is equal to two times a width of said struts plus three times a distance between said struts.

18. The stent-graft of claim 17 wherein said distal apexes are connected to either a pair of said offset struts or a pair of said aligned struts.

19. The stent-graft of claim 17 wherein every other of said distal apexes is connected to a pair of said aligned struts, wherein the distal apexes between said every other of said distal apexes is connected to a pair of said offset struts.

20. The stent-graft of claim 17 wherein said anchor pin connecting short arms are between said anchor pin connecting long arms.

21. The stent-graft of claim 17 wherein a distance between an anchor pin connecting long arm and an adjacent anchor pin connecting short arm is equal to a distance between said struts.

* * * * *

UNITED STATES PATENT AND TRADEMARK OFFICE
CERTIFICATE OF CORRECTION

PATENT NO. : 8,454,682 B2  
APPLICATION NO. : 12/759433  
DATED : June 4, 2013  
INVENTOR(S) : Argentine et al.

Page 1 of 1

It is certified that error appears in the above-identified patent and that said Letters Patent is hereby corrected as shown below:

In the Claims

Column 11, lines 34, 37, 40, 43, and 46

"system of claim 14 wherein"

should be changed to

--system of claim 1 wherein--

Signed and Sealed this  
Fifteenth Day of October, 2013

Teresa Stanek Rea  
*Deputy Director of the United States Patent and Trademark Office*